(12) United States Patent
Pahlck et al.

(10) Patent No.: US 6,528,044 B1
(45) Date of Patent: Mar. 4, 2003

(54) PIGMENTED COSMETIC COMPOSITIONS

(75) Inventors: Harold Pahlck, Waldwick, NJ (US);
Christian J. Lee, Parsippany, NJ (US);
Dennis Cupolo, Suffern, NY (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 10/033,489

(22) Filed: Dec. 27, 2001

(51) Int. Cl.$^7$ .............................. A61K 7/04; A61K 7/00

(52) U.S. Cl. ........................................ 424/61; 424/401

(58) Field of Search ..................................... 424/401, 61

(56) References Cited

U.S. PATENT DOCUMENTS 5,599,530 A * 2/1997 Patil et al. ..................... 424/63

* cited by examiner

Primary Examiner—Theodore J. Criares
Assistant Examiner—Jennifer Kim
(74) Attorney, Agent, or Firm—Ohlandt, Greeley, Ruggiero & Perle, LLP

(57) ABSTRACT

The present invention relates to cosmetic compositions that include one or more laked pigments. The present invention relates to improved cosmetic compositions having one or more laked pigments that include one or more metal salts. The present invention also relates to a method of improving compositions that have one or more laked pigments.

9 Claims, 3 Drawing Sheets

(1 of 3 Drawing Sheet(s) Filed in Color)

PIGMENTED COSMETIC COMPOSITIONS

BACKGROUND OF THE INVENTION

1. Field of the Invention

The present invention relates to colored cosmetic compositions. More particularly, the present invention relates to improved color compositions having one or more pigments, especially laked pigments. The color composition may be a blush, a foundation, a lipstick, or a nail enamel.

The present invention further relates to methods to prevent the conversion of laked pigments to their dye counterparts. More particularly, the present invention relates to methods of reducing color-shift in a cosmetic composition; reducing staining on a nail due to colored nail enamels; and/or improving or increasing stability of a cosmetic composition.

2. Description of the Prior Art

Colored cosmetic compositions are known in the art. Instability of colored cosmetic compositions with respect to changes in the color over time is particularly undesirable by both cosmetic manufacturers and consumers. Consumers who purchase a particular colored cosmetic based upon its color are disappointed when the cosmetic later becomes a different color/shade. When this happens, it reflects negatively on the manufacturer. In addition, colored cosmetic compositions that are unstable present logistical concerns to manufacturers. If a cosmetic composition is unstable in any way, the manufacturer has a shorter period of time for shipping and storing. Moreover, the cosmetic composition will have a shorter shelf-life. Consumers and manufacturers desire and would benefit from compositions that have improved stability, particularly with respect to color change/shift and susceptibility to such color change/shift.

In addition, when colored nail enamels are worn, especially in direct contact with the nails, for an extended period of time, the nail often becomes stained, especially when the nail enamel is a darker and/or deeper color, e.g., red, burgundy or brown. To avoid such staining, consumers are presently inconvenienced by having to apply a primer/base coat to the nail prior to applying the colored nail enamel.

Consumers and cosmetic composition manufacturers desire and would benefit from cosmetic compositions and/or methods that decrease the color shift that occurs in colored compositions, and/or nail enamel compositions that result in decreased staining of nails. These benefits are provided by the compositions and methods of the present invention.

SUMMARY OF THE INVENTION

It is an object of the present invention to provide a color composition having a metal salt in an amount effective to prevent, reduce and/or inhibit the conversion of a laked pigment.

It is another object to provide a method of preventing, reducing and/or inhibiting the conversion of a laked pigment to a dye.

It is still another object of the present invention to provide a method of preventing, reducing and/or inhibiting color shift or color loss of a color composition.

It is another object to provide a method of prevention, reduction and/or inhibition of staining the surface of a nail due to direct contact with a nail enamel over an extended period of time.

These and other objects and advantages of the present invention are achieved by preconditioning a cosmetic base with an amount of a metal salt effective to prevent or inhibit the conversion of a laked pigment.

BRIEF DESCRIPTION OF THE DRAWINGS

The patent or application file contains at least one drawing executed in color. Copies of this patent or patent application publication with color drawing(s) will be provided by the office upon request and payment of the necessary fee.

DETAILED DESCRIPTION OF THE INVENTION

Figure 1:
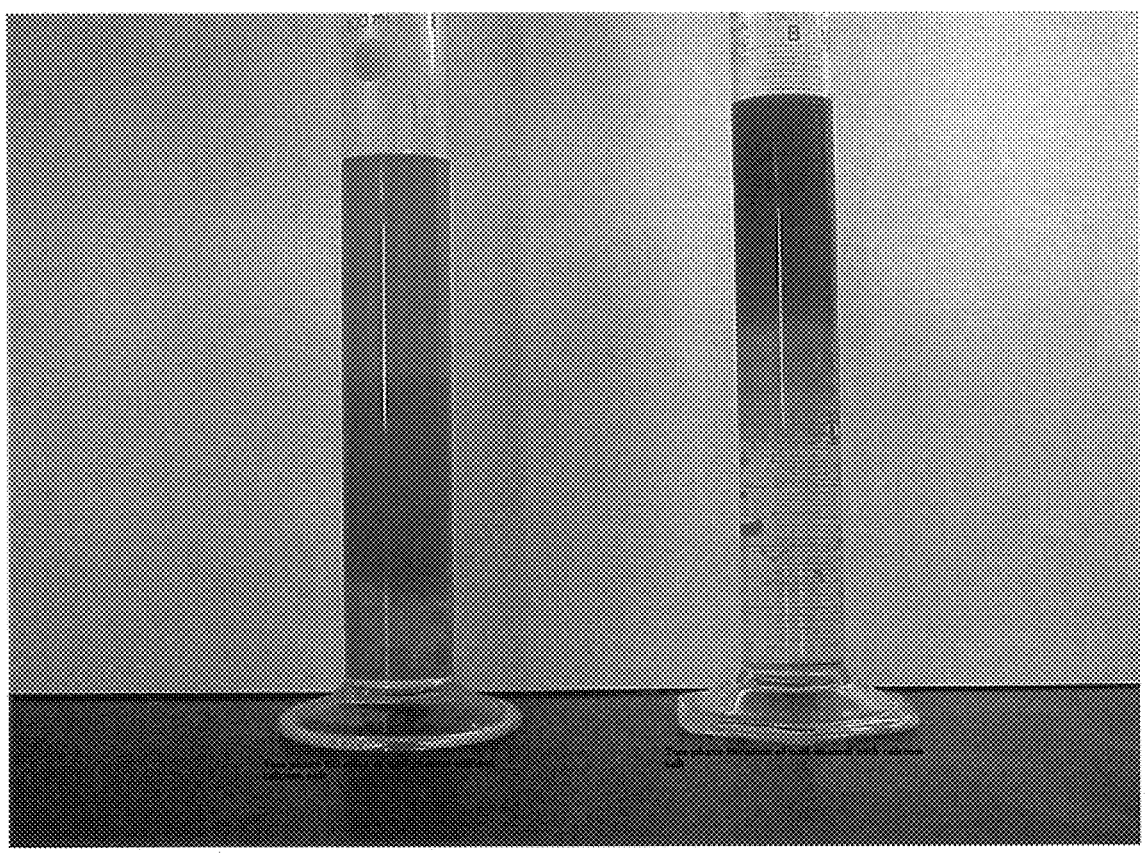
FIG. 1 is a color photograph of two graduated cylinders illustrating the two-phase titration test described in Example 1. A prior art composition is on the left, whereas a composition of the present invention is on the right.
Figure 2:
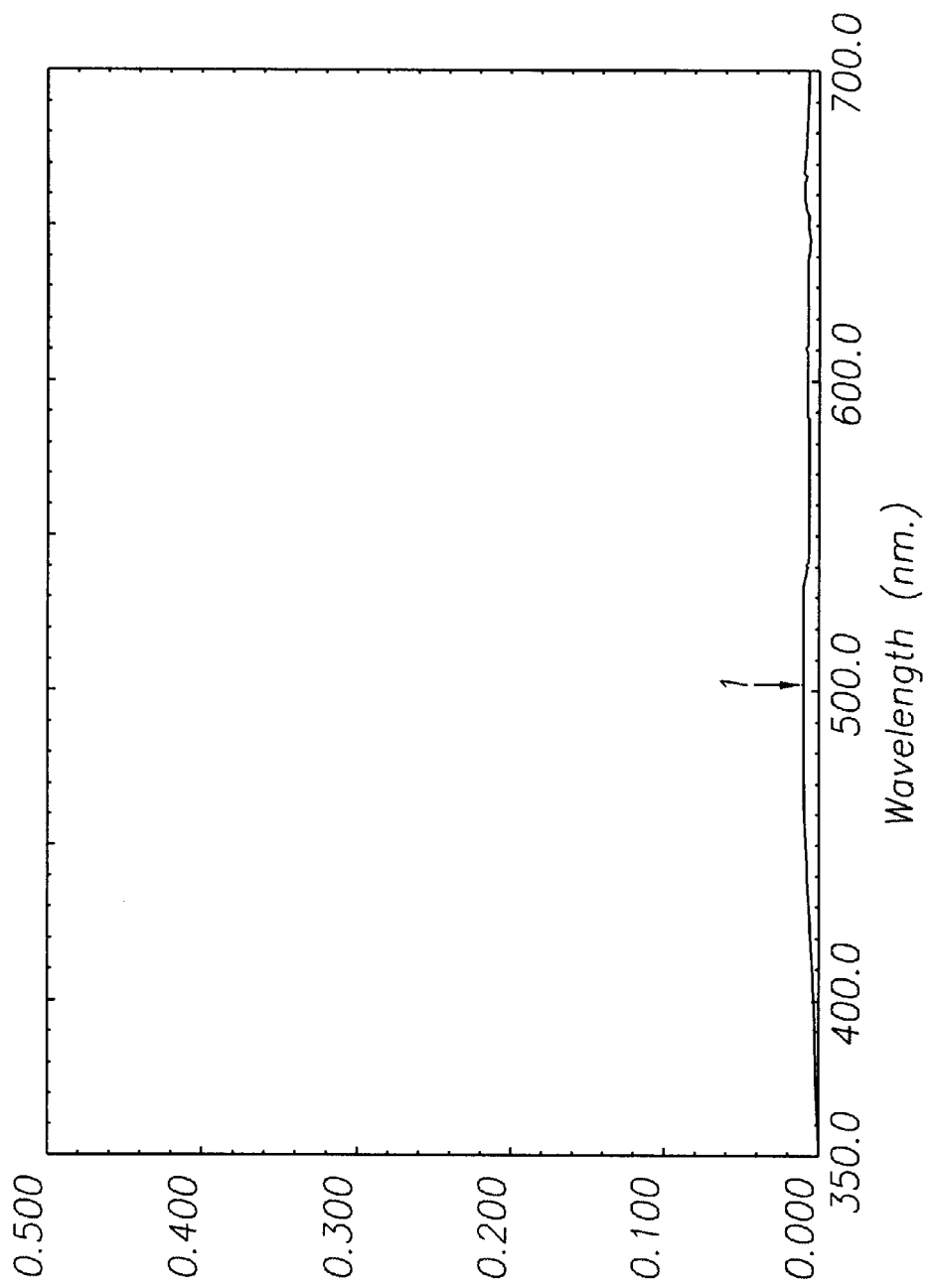
FIG. 2 is a graph illustrating the level of absorbance measured in the aqueous phase of the two-phase titration test depicted in FIG. 1 for a colored composition of present invention.
Figure 3:
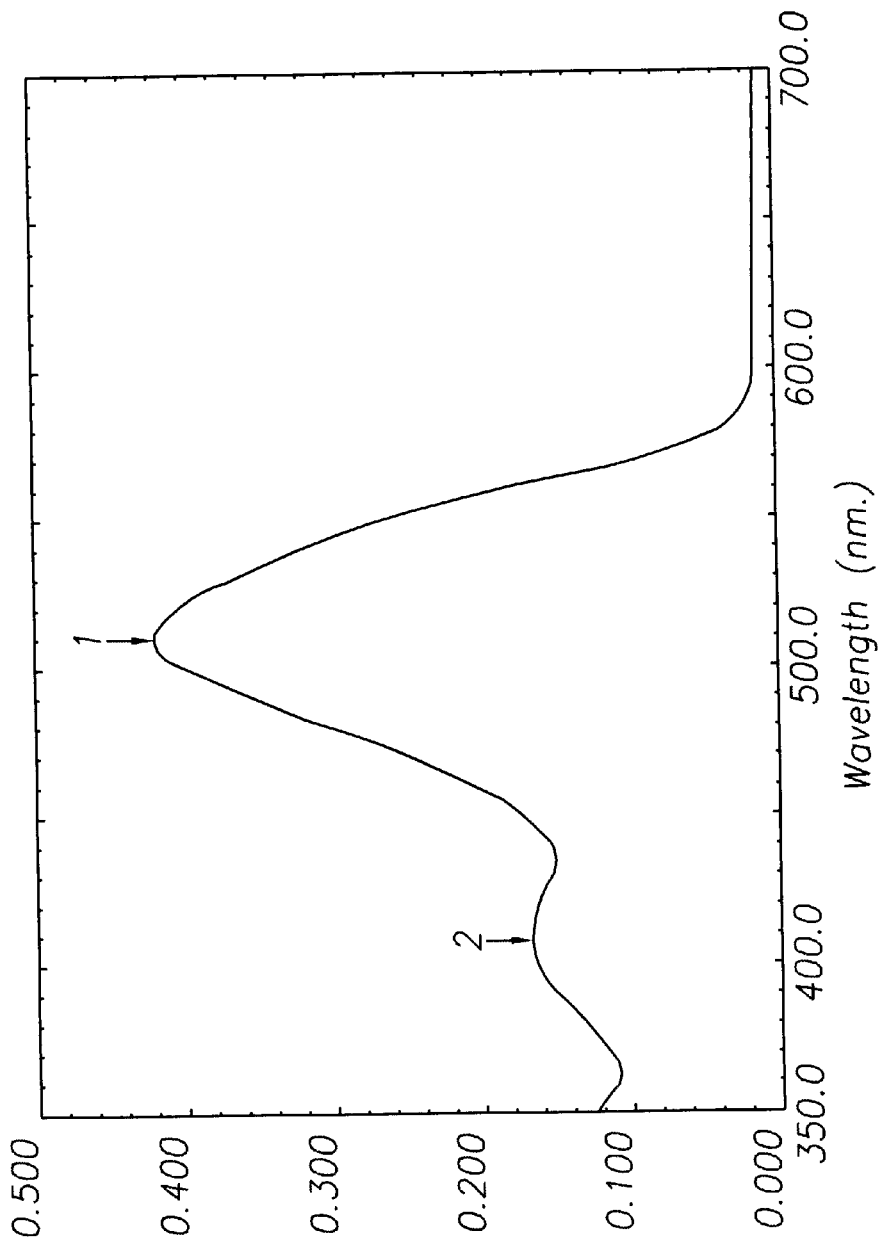
FIG. 3 is a graph illustrating the level of absorbance measured in the aqueous phase of the two-phase titration test depicted in FIG. 1 for a composition of a prior art colored composition.

The present invention relates to colored compositions that include laked pigments. "Laked pigments" are hybrid pigments. Generally, the term "pigment" refers to colorants that are insoluble. Generally, a "dye" is soluble in its medium, which is usually water or at least hydrophilic.

Pigments are more useful in the colored cosmetic industry for various reasons. For one reason, dyes are soluble in the medium, and solubility is associated with increased instability. Over time, this instability may result in degradation of the dye, resulting in fading of the color. To make dyes more insoluble, the dyes are "laked," according to methods known in the art, to form "laked pigments". Laked pigments may be formed by subjecting dyes to an ion exchange to form an organic salt. As a result, laked pigments are hybrid pigments that have a dye component. A non-limiting example of such a laked pigment includes calcium lakes, such as Red No. 7 and Red No. 34.

Over time and especially in polar solvents, a laked pigment may convert to a dye. This conversion may occur for several reasons. It is believed that polar ingredients in the composition may extract the original ion from the laked pigment. Depending upon the other ingredients in the composition, a dye may result or another ion may be substituted and a different laked pigment might form. In any event, the composition no longer has its original color.

This conversion of the laked pigment has more than one negative effect. While the shift incolor from the original intended color is undesirable, when the conversion results in a dye, the increased solubility of the dye in the solvent magnifies the color shift since the dye is now spread throughout the formulation. In addition, the shift in a nail enamel from a laked pigment to a dye increases the tendency of the nail enamel to stain the nail when left in direct contact with the nail for an extended period of time.

Even the conversion of the original laked pigment into a different laked pigment is not without detriment. For example, a colored composition might include a calcium laked pigment (e.g., calcium lake red. No. 7) that imparts a bright cherry red to the composition. Even if the calcium is replaced with a sodium ion, a change in color still occurs. This is undesirable.

The inventors found unexpectedly that the conversion of the desired laked pigment may be prevented, reduced.and/or inhibited (herein all are individually and collectively called "inhibited" or "inhibit" or "inhibiting") by preconditioning a cosmetic base before introducing the laked pigment. While the inventors do not wish to be bound by any one theory, it is believed that when an effective amount of a metal salt is added to the cosmetic base prior to the addition of the laked pigment, the metal salt either (1) reacts with ingredients in the base that would otherwise react with the raked pigment and, thus, cause the conversion of the laked pigment to the dye, or (2) changes the equilibrium of the cosmetic base such that the ion of the pigmented lake is less likely to disengage from the laked pigment.

It is important that the cosmetic base is preconditioned prior to the addition of the laked pigment. It has been found that addition of the metal salt to a colored composition in which the laked pigment has already converted will not result reversal of the conversion to restore the laked pigment to it original state.

Examples of metal salts that can be used in the present compositions include a calcium salt such as calcium alkanoate, calcium acetate, calcium chloride, calcium nitrate, calcium isobutyrate, or any combinations thereof. When the metal salt is a calcium salt, calcium alkanoate and calcium acetate are preferred.

When the composition is a nail enamel and the metal salt is calcium alkanoate, the metal salt is preferably present in an amount about 0.01 weight percent or percentage by weight (wt %) to about 0.5 wt %, and more preferably about 0.01 to less than about 0.2 wt %, of the total weight of the composition. Less than an effective amount of metal salt will lead to slight fading of the laked pigment, while too much metal salt may result in precipitation of the laked pigment. Higher levels of metal salt are associated with detrimental aesthetic and physical properties of cosmetic compositions. For example, too much metal salt in a nail enamel may result in less desirable aesthetics, such as diminished gloss and/or rheology modifier instability, especially when the rheology modifier is stearylalkonium hectoride. Also, too much of the metal salt may lead to precipitation of the metal salt and/or grittiness of the composition.

The amount of metal salt used in the present invention may be modified by those skilled in the art. For example, if a first metal salt that has a higher molecular weight, e.g., calcium alkanoate, is substituted for a second metal salt that has the same stoichiometry, e.g., calcium chloride, the weight percent of the first metal salt should be increased accordingly. Also, if the composition includes a greater number of ingredients (e.g., nitrocellulose, polyurethanes) that exacerbate the conversion of a laked pigment, then the amount of metal salt should be increased accordingly.

The present invention is further illustrated in Example 1.

EXAMPLE

The procedure for the two-phase titration method is as follows.

1. Add 60 mls. of deionized water into a volumetric cylinder ("graduated cylinder").

2. Add 30 gms. of ethyl acetate into the same graduated cylinder.

3. Add color solution of monochromatic nail enamel.

4. Cap the graduated cylinder, shake vigorously for 15 seconds and then let stand and observe.

A conventional nail enamel was added to a graduated cylinder and subjected to two-phase titration (Sample I). To a second graduated cylinder was added the same original nail enamel, but which was first treated with a calcium salt solution (2% by weight) according to the present invention (Sample II).

As illustrated in FIG. 1, Sample I (left) exhibits a noticeable reddish hue in the aqueous phase demonstrating that the laked pigment has converted to a water-soluble dye. The change in color of the water phase is due to converted dye and free dye (previously attached to the laked pigment) leaching into aqueous phase. In contrast, Sample II (right), which contains the calcium salt, does not "leach out" any noticeable dye into the aqueous phase. In addition, Sample I has a more orange hue as compared to Sample II, which has a darker more red hue.

A small volume of the aqueous phase was then removed from each graduated cylinder and using a UV-visible spectrophotometer (model UV-1601 made by Shimadzu) the absorbance was measured. A lower absorbance value reflects that less dye is present in the aqueous phase.

Absorbance data using a UV-visible spectrometer are as follows:

| Sample | Wavelength (nm) | Absorbance |
| --- | --- | --- |
| I | 513 | 0.4203 |
| II | 502 | 0.0104 |

FIG. 1 illustrates the absorbance of Sample II, which is a marked reduction in absorbance that occurs upon spectroscopy testing as compared to the absorbance demonstrated by the aqueous phase of the two-phase titration system of a conventional nail enamel, i.e., Sample I.

The present invention is useful in a broad range of color-cosmetic composition product forms that include, but are not limited to, a blush, a foundation, a lipstick, and a nail enamel. Among these types of cosmetic compositions envisioned by the present invention, it should be noted that shades of red are especially benefited by the present invention since such red colored laked pigments are particularly susceptible to conversion. Also, red laked pigments are typically used in small quantities. Thus, any small change in the color of these laked pigments is magnified and has a large impact on the overall color of the cosmetic composition.

In another embodiment of the present invention, the present invention provides a nail enamel composition that does not stain the nail even after direct contact with the nail for an extended period of time. The term "extended" in the present invention refers to a time period greater than about 1 week, and more preferably greater than about 2 weeks. The term "extended" includes when a first application of nail enamel has been removed and replaced with another nail enamel within the same day.

As was described above and illustrated in Example 1, the ability of the present invention to inhibit the conversion of laked pigments decreases the color shift of a cosmetic composition, especially over time. However, when a laked pigment converts to a dye, the hydrophilic property of the dye leads to a higher degree of staining of the nail, especially when the nail enamel is in direct contact with the nail, and especially when the direct contact is for a period of time greater than about two weeks.

Thus, preconditioning a nail enamel cosmetic base with the metal salt provides a useful method of inhibiting the staining of the nail.

It should be understood that the foregoing description is only illustrative of the present invention. Various alternatives and modifications can be devised by those skilled in the art without departing from the present invention. Accordingly, the present invention is intended to embrace all such alternatives, modifications and variations that fall within the scope of the appended claims.

What is claimed is:

1. A method of inhibiting staining of a nail from a nail enamel comprising applying to the nail a nail enamel composition having at least one laked pigment and about 0.01 to about 0.5 wt % of a metal salt based on the total weight of the composition, wherein the metal salt is present in an amount effective to inhibit conversion of the laked pigment to a dye.

2. The method of claim 1, wherein the nail enamel has been in direct contact with the nail for a period of time greater than one week.

3. The method of claim 1, wherein the nail enamel has been in direct contact with the nail for a period of time greater than two weeks.

4. The method of claim 1, wherein the amount of metal salt is about 0.01 wt % to less than about 0.2 wt % of the total weight of the cosmetic composition.

5. The method of claim 1, wherein the metal salt is a calcium salt.

6. The method of claim 5, wherein the calcium salt is selected from the group consisting of calcium alkanoate, calcium acetate, calcium chloride, calcium nitrate, calcium isobutyrate, and any combinations thereof.

7. The method of claim 4, wherein the at least one metal salt is a calcium salt.

8. The method of claim 7, wherein the calcium salt is selected from the group consisting of calcium alkanoate, calcium acetate, calcium chloride, calcium nitrate, calcium isobutyrate, and any combinations thereof.

9. The method of claim 8, wherein the calcium salt is selected from the group consisting of calcium alkanoate, calcium acetate, and any combination thereof.

* * * * *